United States Patent [19]

Pickart

[11] Patent Number: 5,120,831

[45] Date of Patent: * Jun. 9, 1992

[54] METAL-PEPTIDE COMPOSITIONS

[75] Inventor: Loren R. Pickart, Bellevue, Wash.

[73] Assignee: ProCyte Corporation, Redmond, Wash.

[ * ] Notice: The portion of the term of this patent subsequent to May 12, 2004 has been disclaimed.

[21] Appl. No.: 436,382

[22] Filed: Nov. 13, 1989

Related U.S. Application Data

[63] Continuation-in-part of Ser. No. 442,440, Sep. 22, 1989, which is a continuation of Ser. No. 48,444, May 11, 1987, abandoned, which is a continuation-in-part of Ser. No. 699,824, Feb. 8, 1985, Pat. No. 4,665,054.

[51] Int. Cl.⁵ .................... A61K 37/02; C07K 5/08
[52] U.S. Cl. .................................. 530/331; 514/6; 514/18; 514/17; 514/16; 530/329; 530/330
[58] Field of Search .................... 514/6, 18, 16, 17; 530/331, 330, 329

[56] References Cited

U.S. PATENT DOCUMENTS

| | | | |
|---|---|---|---|
| 3,194,732 | 7/1965 | Neuhauser | 167/58 |
| 3,551,554 | 12/1970 | Herschler | 424/7 |
| 3,558,770 | 1/1971 | Gordon et al. | 424/80 |
| 3,758,682 | 9/1973 | Huber et al. | 424/177 |
| 3,767,784 | 10/1973 | Gluck | 424/28 |
| 3,832,338 | 8/1974 | Huber et al. | 260/113 |
| 4,022,888 | 5/1977 | Huber et al. | 424/177 |
| 4,167,945 | 9/1979 | Gottlieb | 128/334 R |
| 4,177,261 | 12/1979 | Dietze et al. | 424/101 |
| 4,263,428 | 4/1981 | Apple et al. | 536/17 A |
| 4,287,184 | 9/1981 | Young | 424/177 |
| 4,440,788 | 4/1984 | Terayama et al. | 424/320 |
| 4,665,054 | 5/1987 | Pickart | 530/331 |
| 4,760,051 | 7/1988 | Pickart | 514/6 |
| 4,767,753 | 8/1988 | Pickart | 514/18 |

FOREIGN PATENT DOCUMENTS 0078228 4/1982 European Pat. Off. .
86/00222 1/1986 PCT Int'l Appl. .

OTHER PUBLICATIONS

Poole et al., "Stimulation of Rat Peritoneal Mast Cell Migration by Tumor–Derived Peptides," *Cancer Research* 43: 5857–5861, 1983.

Raju et al., "Ceruloplasmin, Copper Ions, and Angiogenesis," *JNCI* 69(5): 1183–1188, 1982.

Freedman et al., "Structure of the Glycyl-L-Histidyl-L-Lysine-Copper(II) Complex in Solution," *Biochemistry* 21: 4540–4544, 1982.

Kwa et al., "PMR Studies of Cu(II) and Zn(II) Interaction with Glycyl-L-Histidyl-L-Lysine and Related Peptides," *Peptides: Structure and Function* 8: 805–808, 1983.

Perkins et al., "The Structure of a Copper Complex of the Growth Factor Glycyl-L-Histidyl-L-Lysine at 1.1 A Resolution," *Inorganica Chimica Acta* 82: 93–99, 1984.

Kimoto et al., "Enhancement of Antitumor Activity of Ascorbate Against Ehrlich Ascites Tumor Cells by the Copper: Glycylglycylhistidine Complex," *Cancer Research* 43: 824–828, 1983.

(List continued on next page.)

Primary Examiner—Lester L. Lee
Attorney, Agent, or Firm—Seed and Berry

[57] ABSTRACT

There is provided metal-peptide compositions for use as stimulating agents for hair growth in warm-blooded animals. Methods for stimulating the growth of hair in warm-blooded animals are also disclosed. The methods utilize a stimulating effective amount of the metal-petide composition or a pharmaceutical preparation containing the metal-peptide composition.

10 Claims, 8 Drawing Sheets

OTHER PUBLICATIONS

Sorenson, "Copper Complexes: A Physiologic Approach to Treatment of Chronic Diseases," *Comprehensive Therapy* 11(4): 49–64, 1985.

Pickart et al., "Inhibition of the Growth of Cultured Cells and an Implanted Fibrosarcoma by Aroylhydrazone Analogs of the Gly-His-Lys-Cu(II) Complex," *Biochem. Pharmacol.* 32(24): 3868–3871, 1983.

Pickart et al., "Growth-Modulating Plasma Tripeptide May Function By Facilitating Copper Uptake Into Cells," *Nature* 288: 715–717, 1980.

Newsreport on Use of GGH-Cu(II) and Ascorbic Acid, *Natural Healing Annual* 1986, p. 38 (M. Bricklin (ed.), Prevention Magazine, Rodale Press, Emmaus, Pa.).

Pickart et al., "A Synthetic Tripeptide which Increases Survival of Normal Liver Cells, and Stimulates Growth in Hepatoma Cells," *Biochem. Biophys. Res. Commun.* 54(2): 562–566, 1973.

Aonuma et al., "Studies on Anti-Ulcerogenic Protein in Inflamed Rabbit Skin Tissues," *Yakugaku Zasshi* 104(4): 362–373, 1984.

Downey et al., "Acceleration of Wound Healing Using GHL-Cu(II)," *Surgical Forum* 36: 573–575, 1985.

Pickart et al., "A Human Plasma Growth Factor with Superoxide Dismutase-Like and Wound-Healing Properties," Superoxide Dim. Chem., Biol. Med. Proc. Int. Conf., 4th 1985 (Pub. 1986), 555–557 (cited in *Chem. Abstracts* 106: 13579c).

Frater-Schroder et al., "Tumor Necrosis Factor Type a, a Potential Inhibitor of Endothelial Cell Growth in vitro is Angiogenic in vivo," *Proc. Natl. Acad. Sci. U.S.A.* 34: 5277–5281, 1987.

Pickart, "The Use of Glycylhistidyllysine in Culture Systems," *In Vitro* 17(6): 459–466, 1981.

METAL-PEPTIDE COMPOSITIONS

CROSS-REFERENCE TO RELATED APPLICATIONS

This application is a continuation-in-part of U.S. Ser. No. 07/442,440, filed Sep. 22, 1989, which application is a continuation of U.S. Ser. No. 048,444, filed May 11, 1987, now abandoned, which is a continuation-in-part of U.S. Ser. No. 699,824, filed Feb. 8, 1985, which issued as U.S. Pat. No. 4,665,054 on May 12, 1987.

TECHNICAL FIELD

The present invention relates to the stimulation of hair growth with metal-peptide compositions in general and, more specifically, to the use of metal chelates of glycyl-L-histidyl-L-lysine, L-lysyl-L-histidyl-glycine and derivatives thereof in the stimulation of hair growth in warm-blooded animals.

BACKGROUND OF THE INVENTION

Hair loss is a common affliction of humans, the most typical being "alopecia" where males lose scalp hair with age (male pattern baldness). Hair is normally divided into two types, "terminal" and "vellus" hairs. Terminal hair is coarse, pigmented hair which arises from follicles which are developed deep within the dermis. Vellus hair is typically thin, non-pigmented hair which grows from hair follicles which are smaller and located superficially in the dermis. As alopecia progresses, there is a general change from terminal to vellus type hair.

Other changes associated with alopecia are alterations in the growth cycle of hair. Hair typically progresses through three cycles, anagen (active hair growth phase), catagen (transition phase), and telogen (resting phase during which the hair shaft is shed prior to new growth). As baldness progresses, there is a shift in the percentages of hair follicles in each phase, with the majority shifting from anagen to telogen. The size of hair follicles is also known to decrease while the total number remains relatively constant.

A common treatment for the loss of hair has been hair transplantation. Briefly, plugs of skin containing hair are transplanted from areas of the scalp where the hair is growing to bald areas. This procedure is a costly one, in addition to being time-consuming and relatively painful. Other treatments have included ultraviolet radiation and exercise therapy. However, these have not been generally accepted as being effective.

In addition to hair transplants, the most common approach to stimulating hair growth has been in the area of drug therapy. However, the use of drugs in this regard has met with only limited success. One of the most promising compositions for stimulating the growth of hair is disclosed by Upjohn in U.S. Pat. No. 4,596,812, which describes the use of a substance commonly known as "Minoxidil" for treating male pattern baldness. However, while the results generated through the use of Minoxidil have appeared promising, there is still a need in the art for improved compositions capable of stimulating the growth of hair in warm-blooded animals. The present invention fulfills this need, while further providing other related advantages.

DISCLOSURE OF THE INVENTION

Briefly stated, the present invention provides metal-peptide compositions and derivatives thereof for use as stimulating agents for the growth of hair in warm-blooded animals.

The present invention also provides methods for stimulating hair growth in warm-blooded animals by administering to the animal a stimulatory effective amount of the metal-peptide composition or a pharmaceutical preparation containing the metal-peptide composition.

The metal-peptide compositions described herein include metal ion chelates of glycyl-L-histidyl-L-lysine (GHL), L-lysyl-L-histidyl-glycine (LHG), and various derivatives of GHL and LHG. The metal ions include copper(II), cadmium (II), cobalt (II), tin (II), iron (II), manganese (II), and the like. Thus, if copper(II) serves as the metal ion, the corresponding metal-peptide compositions include GHL:copper(II)(GHL-Cu), LHG:copper(II)(LHG-Cu), and derivatives of GHL-Cu and LHG-Cu.

The metal-peptide derivatives of GHL have the general formula:

wherein X is a metal ion selected from the group consisting of copper(II), cadmium (II), cobalt (II), tin (II), iron (II) and manganese (II); and R is selected from the group consisting of an —$NH_2$ moiety, alkyl moieties containing from 1 to 18 carbon atoms, aryl moieties containing from 6 to 12 atoms, alkoxy moieties containing from 1 to 18 carbon atoms, aryloxy moieties containing from 6 to 12 carbon atoms, alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-4.

The metal-peptide derivatives of LHG have the general formula:

wherein X is a metal ion selected from the group consisting of copper(II), cadmium (II), cobalt (II), tin (II), iron (II) and manganese (II); and R is selected from the group consisting of an —$NH_2$ moiety, alkyl moieties containing from 1 to 18 carbon atoms, aryl moieties containing from 6 to 12 carbon atoms, alkoxy moieties containing from 1 to 18 carbon atoms, aryloxy moieties containing from 6 to 12 carbon atoms, alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-4.

In addition to the derivatives described above, other chemical modifications may be made to alter the biological activity of the metal-peptide composition. For instance, glycine may be replaced by a variety of other amino acids, including alanine, serine or valine. Further, in the case of copper(II), the binding affinity of the peptide may be increased by addition of an N-terminal amino acid, such as glycine, to convert, for example, GHL-Cu to glycyl-GHL-Cu. The binding affinity for the metal ion by the imidazole group in the histidyl residue may also be modified by substitution of 3-methylhistidine or by extending the lysyl side chain by adding additional carbon atoms to the chain. Similarly, other molecules may be added to the metal-peptide composition, for example histidine, to form a ternary metal-peptide-histidine complex. Lastly, the D-forms of amino acids may be used in addition to the L-forms.

Other aspects of the present invention will become evident upon reference to the following detailed description and attached drawings.

BRIEF DESCRIPTION OF THE DRAWINGS

FIG. 9 is a photomicrograph of a histological section through a control area (FIG. 9A) and through an area of accelerated hair growth of a mouse injected with glycyl-L-histidyl-L-lysine palmityl ester:copper(II) (FIG. 9B).

DETAILED DESCRIPTION OF THE INVENTION

As described herein, metal ion chelates of GHL, LGH and derivatives thereof may be used in the stimulation of hair growth in warm-blooded animals. Pharmaceutical preparations containing these compounds are also disclosed. Compositions of the present invention are described in detail in U.S. Pat. Nos. 4,760,051; 4,665,054; and 4,877,770; which are incorporated herein by reference.

The metal-peptide derivatives of GHL have the general formula:

[glycyl-L-histidyl-L-lysine-C—R]:X wherein X is a metal ion selected from the group consisting of copper(II), cadmium (II), cobalt (II), tin (II), iron (II) and manganese (II); and R is selected from the group consisting of an —NH$_2$ moiety, alkyl moieties containing from 1 to 18 carbon atoms, aryl moieties containing from 6 to 12 atoms, alkoxy moieties containing from 1 to 18 carbon atoms, aryloxy moieties containing from 6 to 12 carbon atoms, alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-4.

The metal-peptide derivatives of LHG have the general formula:

[L-lysyl-L-histidyl-glycine-C—R]:X wherein X is a metal ion selected from the group consisting of copper(II), cadmium (II), cobalt (II), tin (II), iron (II) and manganese (II); and R is selected from the group consisting of an —NH$_2$ moiety, alkyl moieties containing from 1 to 18 carbon atoms, aryl moieties containing from 6 to 12 carbon atoms, alkoxy moieties containing from 1 to 18 carbon atoms, aryloxy moieties containing from 6 to 12 carbon atoms, alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-4.

Within the present invention, one may utilize a ratio of GHL, LHG or derivative thereof to metal ion of 1:1, 2:1 or less. Within a preferred embodiment of the present invention, a ratio of 0.5-0.9 metal atoms per GHL, LHG or derivative thereof is employed. As mentioned above, suitable metal ions include copper(II), cadmium (II), cobalt (II), tin (II), iron (II), manganense (II), and the like. While all of these metal ions show activity when chelated with the peptides of the present invention, copper has exhibited the greatest activity with respect to the stimulation of hair growth.

In one embodiment of the present invention, the pharmaceutical preparations described herein may be administered intradermally in the area to be treated, along with a suitable vehicle, in a concentration of approximately 100-500 micrograms of the metal-peptide composition per 0.1 ml of vehicle. Suitable vehicles in this regard include saline, sterile water, and the like.

In another embodiment, pharmaceutical preparations containing metal ion chelates of GHL, LHG and derivatives thereof may be topically applied in the form of either liquids, lotions, creams or gels. Topical administration of the pharmaceutical preparations of the present invention may be accomplished by applying an amount of the composition directly to a desired area. Any quantity sufficient to accelerate the rate of hair growth is effective and treatment may be repeated as often as the progress of hair growth indicates. Preferable and effective dosages of the preparations of the present invention range from about 0.1% to about 20% by weight of the metal-peptide composition, with a more prefered range being about 1.0% to 10.0% by weight. When used in the form of a cream or gel and applied topically, it is useful to add a suitable penetration enhancing agent (as discussed below) to the composition.

In still another embodiment of the present invention, the topically applied pharmaceutical preparations may contain about 0.5% to about 10% of an emulsifying or surface active agent. Non-ionic surface active agents and ionic surface active agents may be used for the purposes of the present invention. Examples of suitable non-ionic surface active agents are nonylphenoxypolyethoxy ethanol (Nonoxynol-9), polyoxyethylene oleyl ether (Brij-97), various polyoxyethylene ethers (Tritons), and block copolymers of ethylene oxide and propylene oxide of various molecular weights (Pluronic 68, for example). Pharmaceutically acceptable preparations may also contain about 1% to about 10% of certain ionic surface active agents. These ionic surface active agents may be used in addition to or in place of the non-ionic surface active agents. Examples of ionic surface active agents would be sodium lauryl sulfate and similar compounds.

In addition to, or in place of, the emulsifying or surface active agent, the topically applied pharmaceutical preparations may contain about 1% to about 20% of a penetration enhancing agent. Examples of penetrating enhancing agents are dimethyl sulfoxide (DMSO) and urea. In the case of a liquid pharmaceutical preparation to be applied topically, the concentration of a penetrating enhancing agent such as dimethyl sulfoxide (DMSO) may comprise about 30% to about 80% of the pharmaceutical preparation.

The balance of the topically applied pharmaceutical preparations comprise an inert, physiologically acceptable carrier. Suitable carriers include, but are not limited to, water, physiological saline, bacteriostatic saline (saline containing 0.9 mg/ml benzyl alcohol), petrolatum based creams (e.g., USP hydrophilic ointments and similar creams, Unibase, Parke-Davis), various types of pharmaceutically acceptable gels, and short chain alcohols and glycols (e.g., ethyl alcohol and propylene glycol).

The following are examples of suitable pharmaceutical preparations within the context of the present invention:

| Pharmaceutical Preparation A: | | |
|---|---|---|
| Metal-Peptide Composition | 10.0% | (w/w) |
| Hydroxy Ethyl Cellulose | 3.0% | |
| Propylene Glycol | 20.0% | |
| Nonoxynol-9 | 3.0% | |
| Sodium Lauryl Sulfate | 2.0% | |
| Benzyl Alcohol | 2.0% | |
| 0.2N Phosphate Buffer | 60.0% | |
| Pharmaceutical Preparation B: | | |
| Metal-Peptide Composition | 10.0% | (w/w) |
| Nonoxynol-9 | 3.0% | |
| Ethyl Alcohol | 87.0% | |
| Pharmaceutical Preparation C: | | |
| Metal-Peptide Composition | 5.0% | (w/v) |
| Ethyl Alcohol | 47.5% | |
| Isopropyl Alcohol | 4.0% | |
| Propylene Glycol | 20.0% | |
| Laoneth-4 | 1.0% | |
| Water | 22.5% | |
| Pharmaceutical Preparation D: | | |
| Metal-Peptide Composition | 5.0% | (w/v) |
| Sterile Water | 95.0% | |
| Pharmaceutical Preparation E: | | |
| Metal-Peptide Composition | 5.0% | (w/v) |
| Hydroxypropyl Cellulose | 2.0% | |
| Glycerine | 20.0% | |
| Nonoxynol-9 | 3.0% | |
| Sterile Water | 70.0% | |
| Pharmaceutical Preparation F: | | |
| Metal-Peptide Composition | 1.0% | (w/w) |
| Nonocynol-9 | 5.0% | |
| -continued | |
|---|---|
| Unibase Cream | 94.0% |

Figure 1:
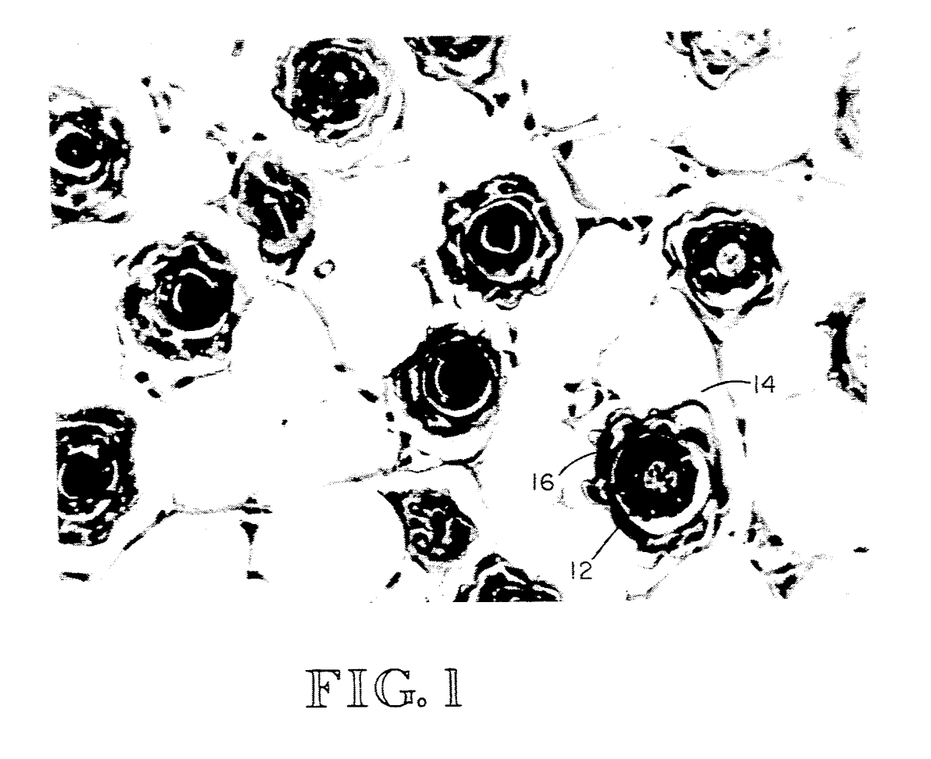
FIG. 1 is a photomicrograph showing the histology of an area of enhanced hair growth following treatment with a composition of the present invention.

Use of the derivatives as described herein are illustrated in FIG. 1, which is a photomicrograph showing the histology of an area of enhanced hair growth. More specifically, as shown in FIG. 1, the hair follicles 12 (dark objects) are embedded in a heavy field of large, subcutaneous fat cells 14 (white rounded cells) surrounded by blood capillaries 16. The enhancement of subcutaneous fat (adipocyte formation) in areas associated with increased hair growth is highly significant. Increased adipocyte formation, is spatially and temporally linked with hair follicle formation, and is an integral phase of hair follicle formation (Hausman et al., Am. J. Anat. 161:85–100, 1981). Moreover, male pattern baldness is intimately associated with a dramatic reduction in the amount of subcutaneous fat associated with hair follicles that are nonproductive. Conversely, during periods of rapid hair growth in mammals, the subcutaneous fat content increase two- to threefold.

Therefore, derivatives of the present invention have clinical use in at least three primary areas: (1) the direct stimulation of hair growth in persons with hair loss, (2) the stimulation of hair transplants, and (3) increasing the subcutaneous fat content.

As noted above, the compositions of the present invention include metal ion chelates of GHL, LHG, or derivatives thereof. The overall chemical reaction in the synthesis of GHL derivatives may be characterized:

$$GHL-OH + R-H \rightarrow GHL-R + H_2O.$$

The reaction is most readily carried out by adding the R group to the amino acid lysine prior to the combination of lysine with the other two amino acids to GHL. After the formation and isolation of GHL-R, the metal ion is chelated to the molecule to form the bioactive complex.

The overall reaction to form the more lipophilic derivatives of GHL-X (where X is the metal ion) may be characterized:

1) lysine-OH + R—H → lysine-R + H$_2$O
2) lysine-R + blocked L-histidine → blocked L-histidine-L-lysine-R
3) blocked L-histidine-L-lysine-R → partially blocked L-histidine-L-lysine-R
4) partially blocked L-histidine-L-lysine-R + blocked glycine → blocked glycyl-L-histidine-L-lysine-R
5) blocked glycyl-L-histidine-L-lysine-R → glycyl-L-histidine-L-lysine-R
6) glycyl-L-histidine-L-lysine-R + X → glycyl-L-histidine-L-lysine-R:X.

The overall reaction to form derivatives of LGH-X is the same as outlined above for GHL-X, except glycine-OH is the initial reaction component instead of lysine-OH and blocked lysine is used in place of blocked glycine in step 4.

To summarize the examples which follow, Examples 1-5 illustrate the synthesis of GHL derivatives. Example 1 is a synthesis of glycyl-L-histidyl-L-lysine benzyl ester:copper(II). Example 2 demonstrates the synthesis of glycyl-L-histidyl-L-lysine n-octyl ester:copper(II). Example 3 illustrates the synthesis of glycyl-L-histidyl-L-lysine n-stearyl ester:copper(II). Based upon this procedure, one skilled in the art could substitute n-palmityl alcohol (16 carbons) for the n-stearyl alcohol (18 carbons) to yield glycyl-L-histidyl-L-lysine n-palmityl ester:copper(II). Example 4 illustrates the synthesis of glycyl-L-histidyl-L-lysyl-L-prolyl-L-phenylalanyl-L-valine:copper(II) and glycyl-L-histidyl-L-lysyl-L-valyl-L-phenylalanyl-L-valine:copper(II). Example 5 illustrates the synthesis of L-lysyl-L-histidyl-glycine n-octyl amide.

Examples 6-9 illustrate the synthesis of LHG and derivatives thereof. Example 6 illustrates the synthesis of L-lysyl-L-histidyl-glycine amide. Example 7 illustrates the synthesis of L-lysyl-L-histidyl-glycine amide. Example 8 illustrates the synthesis of octyl L-lysyl-L-histidyl-glycinate. Example 9 demonstrates the multigram synthesis of L-lysyl-L-histidyl-glycyl-L-valyl-L-phenylalanyl-L-valine.

Example 10 illustrates stimulated and accelerated hair growth in mice by glycyl-L-histidyl-L-lysyl-L-valyl-L-phenylalanyl-L-valine:copper(II). Example 11 illustrates stimulated and accelerated hair growth by glycyl-L-histidyl-L-lysine octyl ester complexed with various metal ions. Example 12 illustrates the stimulation and acceleration of hair growth by L-lysyl-L-histidyl-glycine octyl ester:copper(II) and L-lysyl-L-histidyl-glycyl-L-valyl-L-phenylalanyl-L-valine:copper(II). Example 13 illustrates stimulated and accelerated hair growth by topical application of glycyl-L-histidyl-L-lysyl-L-valyl-L-phenylalanylvaline:copper(II). Example 14 illustrates the stimulation and acceleration of hair growth by glycyl-L-(3-methyl)-histidyl-L-lysyl-L-glycyl-L-tryptophan. Example 15 illustrates the stimulation and acceleration of hair growth by glycyl-L-histidyl-L-lysine n-octyl ester:copper(II). Example 16 illustrates the stimulation and acceleration of hair growth by glycyl-L-histidyl-L-lysine decyl ester:copper(II). Example 17 illustrates the stimulation and acceleration of hair growth by glycyl-L-histidyl-L-lysine palmityl ester:copper(II).

The following examples are offered by way of illustration and not by way of limitation.

EXAMPLES

Sources of Chemicals

Chemicals and peptide intermediates utilized in the above examples may be purchased from a number of suppliers, for example: Sigma Chemical Co., St. Louis, Mo.; Peninsula Laboratories, San Carlos, Caif.; Aldrich Chemical Company, Milwaukee, Wis.; Vega Biochemicals, Tucson, Ariz.; Pierce Chemical Co., Rockford, Ill.; Research Biochemicals, Cleveland, Ohio; Van Waters and Rogers, South San Francisco, Caif.; and Bachem, Inc., Torrance, Caif.

Preparation of peptide and peptide analog metal complex

Metal complexes of GHL, LGH and derivatives thereof can be prepared in any molar ratio by the addition of a required molar amount of ultra pure metal chloride (e.g., 99.999% available from Chemical Dynamics, N.J.) to GHL, LGH, or derivatives thereof in solution in distilled water. After the addition of the metal chloride, the pH of the solution is adjusted to approximate neutrality. Any precipitate formed can be removed by centrifugation and filtration by the usual means. Metal salts other than chloride may also be used, for example, acetate, sulfate, or nitrate salts.

EXAMPLE 1

Synthesis of glycyl-L-histidyl-L-lysine benzyl ester:copper(II)

$N^e$-benzyloxycarbonyl-L-lysine benzyl ester was dissolved in 1:1 hexane-ethyl acetate and coupled to $N^a$-t-butyloxycarbonyl-$N^{im}$-benzyloxycarbonyl-L-histidine using dicyclohexylcarbodiimide as a coupling agent. Sodium bicarbonate (10%) was added and the product was extracted into the organic layer. The product, $N^a$-t-butyloxycarbonyl-$N^{im}$-benzyloxycarbonyl-L-histidyl-$N^e$-benzyloxycarbonyl-L-lysine benzyl ester, was crystallized from solution. The N-terminal group of the blocked dipeptide was removed by stirring in 50% trifluoroacetic acid in dichloromethane for 30 minutes, then vacuum evaporated.

The product, $N^{im}$-benzyloxycarbonyl-L-histidyl-$N^e$-benzyloxycarbonyl-L-lysine benzyl ester, was coupled to t-butyloxycarbonyl-L-glycine with dicyclohexylcarbodiimide as a coupling agent. Blocking groups were removed by catalytic hydrogenation using 10% palladium on carbon in glacial acetic acid. After lyophilization, the product, glycyl-L-histidyl-L-lysine benzyl ester, was dissolved in water and purified by ion-exchange chromatography on Dowex 40 X-4 cation exchange resin and elution with 0.1M ammonium hydroxide, the eluate being immediately neutralized with acetic acid. A further passage through an anion exchange column, BioRex 63, at neutral pH removed breakdown products with free carboxylic acid groups.

The glycyl-L-histidyl-L-lysine benzyl ester was dissolved in water with equimolar copper(II) acetate added. The pH was raised to neutrality with sodium hydroxide. The solution was centrifuged at 20,000× g for 1 hour at 3° C. to remove poorly soluble material. The supernatant solution was lyophilized to obtain glycyl-L-histidyl-L-lysine benzyl ester:copper(II).

EXAMPLE 2

Synthesis of glycyl-L-histidyl-L-lysine octyl ester:copper(II)

A mixture of $N^e$-benzyloxycarbonyl-L-lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitate solid was added to 50 ml of potassium carbonate solution and 50 ml of dichloromethane. After extraction, the layers were separated and the organic phase was washed with water and brine, then dried with anhydrous magnesium sulfate. Filtration, evaporation and purification by flash column chromatography gave n-octyl $N^e$-benzyloxycarbonyl-L-lysine.

The product was dissolved in tetrahydrofuran and mixed with $N^a$-t-butyloxycarbonyl-$N^{im}$-benzyloxycarbonyl-L-histidine, isobutyl chloroformate and N-methylmorpholine. After evaporation, water and ethyl acetate was added. The product was extracted into the organic phase, which was dried with anhydrous magnesium sulfate. Filtration, evaporation, and purification by flash column chromatography gave n-octyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-N$^e$-benzyloxycarbonyl-L-lysinate. This was dissolved in tetrahydrofuran, and isobutyl chloroformate, N-methylmorpholine and benzyloxycarbonylglycine were added to form n-octyl benzyloxycarbonylglycyl-N$^{im}$-benzyloxycarbonyl-L-histidyl-N$^e$-benzyloxycarbonyl-L-lysinate. This was dissolved in glacial acetic acid and hydrogenated overnight.

The resultant n-octyl ester of glycyl-L-histidyl-L-lysine was converted to the copper(II) complex by dissolving water and mixing with equimolar copper(II) acetate. The pH was raised to neutrality with sodium hydroxide. The solution was centrifuged at 20,000× g for 1 hour at 3° C. to remove poorly soluble material. The supernatant solution was lyophilized to obtain glycyl-L-histidyl-L-lysine benzyl octyl:copper(II).

EXAMPLE 3

Synthesis of glycyl-L-histidyl-L-lysine n-stearyl ester:copper(II)

A mixture of N$^e$-benzyloxycarbonyl-L-lysine, n-stearyl alcohol, benzene, and p-toluenesulfonic acid monohydrate was refluxed overnight using a Dean-Stark trap to azeotropically remove the evolved water. After cooling to room temperature and then adding dry ethyl ether, n-stearyl N$^e$-benzyloxycarbonyl-L-lysinate p-toluenesulfonate salt is collected by filtration, treated with 2M aqueous potassium bicarbonate solution, and extracted into dichloromethane. Evaporation gives the free amine, which is redissolved in dry tetrahydrofuran (THF) and added to a stirring solution of N$^a$-t-butyloxycarbonyl-N$^{im}$-benzyloxycarbonyl-L-histidine, N-methylmorpholine, and isobutyl chloroformate in dry THF at −15° C.

The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonylglycine, N-methylmorpholine, and isobutyl chloroformate in dry THF at −15° C. The formed, fully protected tripeptide ester is totally deblocked by treatment with hydrogen gas in glacial acetic acid at room temperature in the presence of Pd-C catalyst. Filtration, evaporation and purification on a microcrystalline cellulose column followed by lyophilization give the desired tripeptide ester as its triacetate salt.

The resulting molecule n-stearyl ester of glycyl-L-histidyl-L-lysine was converted to the copper(II) complex by dissolving in water and mixing with equimolar copper(II) acetate. The pH was raised to neutrality with sodium hydroxide. The solution was centrifuged at 20,000× g for 1 hour at 3° C. to remove poorly soluble material. The supernatant solution was lyophilized to obtain glycyl-L-histidyl-L-lysine benzyl stearyl:copper(II).

By substituting n-palmityl alcohol for the n-stearyl alcohol, glycyl-L-histidyl-L-lysine n-palmityl ester may be similarly synthesized.

EXAMPLE 4

Synthesis of glycyl-L-histidyl-L-lysyl-L-prolyl-L-valyl-L-phenylalanyl-L-valine:copper(II) and glycyl-L-histidyl-L-lysyl-L-valyl-L-phenylalanyl-L-valine:copper(II)

Multi-gram quantity of glycyl-L-histidyl-L-lysyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as coupling agent (2 hours at −20° C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, N$^a$-t-butyloxycarbonyl-N$^e$-benzyloxycarbonyl-L-lysine, N$^a$-t-butyloxycarbonyl-N$^{im}$-benzyloxycarbonyl-L-histidine, benzyloxycarbonylglycine) were added, and t-butyloxycarbonyl protecting groups were removed in sequential order to obtain the desired peptide. The final peptide was completely deprotected using hydrogen gas in acetic acid for 5 days in the presence of 10% Pd-C catalyst. The final peptide was lyophilized from water and purified by liquid chromatography on a C-reverse-phase column to produce the desired hexapeptide in multi-gram quantity.

The resulting hexapeptide glycyl-L-histidyl-L-lysyl-L-valyl-L-phenylalanyl-L-valine was converted to the copper(II) complex by dissolving in water and mixing with equimolar copper(II) acetate. The pH was raised to neutrality with sodium hydroxide. The solution was centrifuged at 20,000× g for 1 hour at 3° C. to remove poorly soluble material. The supernatant solution was lyophilized to obtain glycyl-L-histidyl-L-lysyl-L-valyl-L-phenylalanyl-L-valine:copper(II).

In a similar synthesis, multi-gram quantity of glycyl-L-histidyl-L-lysyl-L-prolyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as coupling agent (2 hours at −20° C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, t-butyloxycarbonyl-L-proline, N$^a$-t-butyloxycarbonyl-N$^e$-benzyloxycarbonyl-L-lysine, N$^a$-t-butyloxycarbonyl-N$^{im}$-benzyloxycarbonyl-L-histidine, benzyloxycarbonylglycine) were added, and t-butyloxycarbonyl protecting groups were removed in sequential order to obtain the desired peptide. The final peptide was completely deprotected using hydrogen gas in acetic acid for 5 days in the presence of 10% Pd-C catalyst. The final peptide was lyophilized from water and purified by liquid chromatography on a C-18 reverse-phase column to produce the desired heptapeptide in multi-gram quantity.

The resulting heptapeptide glycyl-L-histidyl-L-lysyl-L-prolyl-L-valyl-L-phenylalanyl-L-valine was converted to the copper(II) complex by dissolving in water and mixing with equimolar copper(II) acetate. The pH was raised to neutrality with sodium hydroxide. The solution was centrifuged at 20,000× g for 1 hour at 3° C. to remove poorly soluble material. The supernatant solution was lyophilized to obtain glycyl-L-histidyl-L-lysyl-L-prolyl-L-valyl-L-phenylalanyl-L-valine:copper(II).

The above systematic synthesis proved advantageous over some of the solid phase methods in providing multi-gram quantity of the desired peptide in high purity with minimal purification.

EXAMPLE 5

Synthesis of glycyl-L-histidyl-L-lysine n-octyl amide

A solution of $N^\alpha$-t-butyloxycarbonyl-$N^\epsilon$-benzyloxycarbonyl-L-lysine in tetrahydrofuran was treated with N-methylmorpholine, isobutyl chloroformate, and octylamine at −15° C. The resulting fully protecting octyl amide was then treated with ½ trifluoroacetic acid/dichloromethane at room temperature, neutralized with saturated aqueous potassium bicarbonate solution, and extracted into ethyl acetate. Evaporation gave the deblocked lysinamide which was added to a solution prepared from $N^{\alpha\text{-}t\text{-}butyloxycarbonyl\text{-}N^{im}}$-benzyloxycarbonyl-L-histidine, N-methylmorpholine, and isobutyl chloroformate in dry tetrahydrofuran at −15° C.

The fully protected dipeptide formed above was deblocked by treatment with ½ trifluoroacetic acid/dichloromethane at room temperature, followed by neutralization with saturated aqueous potassium bicarbonate. Extraction into ethyl acetate and evaporation gave the partially deblocked dipeptide, which was added to a solution prepared from $N^\alpha$-benzyloxycarbonyl glycine, N-methylmorpholine, and isobutyl chloroformate in dry tetrahydrofuran at −15° C. The resulting protected tripeptide was deblocked by treatment with hydrogen in the presence of 10% palladium on carbon in glacial acetic acid. Filtration and lyophilization gave the title compound as its triacetate salt.

EXAMPLE 6

Synthesis of L-lysyl-L-histidyl-glycine $N^\alpha$-t-butyloxycarbonyl-$N^{im}$-benzyloxycarbonyl-L-histidine was dissolved in tetrahydrofuran (THF) and neutralized with one equivalent of N-methylmorpholine. It was then coupled with benzyl glycinate p-toluenesulfonate salt using isobutyl chloroformate and N-methylmorpholine. After 2 hours at −20° C. and an additional hour at ambient temperature, the reaction was quenched with 2N aqueous potassium bicarbonate. The product was extracted into ethyl acetate, washed with 1M aqueous citric acid, and saturated sodium bicarbonate. The organic phase was dried over anhydrous sodium sulfate. Filtration and evaporation gave benzyl $N^\alpha$-t-butyloxycarbonyl-$N^{im}$-benzyloxycarbonyl-L-histidyl-glycinate.

This product was dissolved in anhydrous methanolic hydrogen chloride (saturated at 0° C.) for 5 minutes, followed by removal of solvent under reduced pressure, forming benzyl $N^{im}$-benzyloxycarbonyl-L-histidyl-glycinate. This was dissolved in tetrahydrofuran, and isobutyl chloroformate, N-methylmorpholine and $N^\alpha,N^\epsilon$-dibenzyloxycarbonyl-L-lysine were added to form benzyl $N^\alpha,N^\epsilon$-dibenzyloxycarbonyl-L-lysine-L-histidyl-glycinate (3 hours at −20° C., then 1 hour at ambient temperature). This product was then dissolved in methanol/acetic acid [1:1 (v/v)] and hydrogenated overnight in the presence of 10% Pd-C catalyst. The resultant L-lysyl-L-histidyl-glycine was lyophilized from water several times, then purified by liquid chromatography on a C-18 reverse-phase column to yield the desired tripeptide triacetate salt as a foamy white solid.

EXAMPLE 7

Synthesis of L-lysyl-L-histidyl-glycine amide $N^\alpha$-t-butyloxycarbonyl-$N^{im}$-benzyloxycarbonyl-L-histidine was dissolved in tetrahydrofuran (THF) and neutralized with one equivalent of N-methylmorpholine. It was then coupled with glycinamide hydrochloride using isobutyl chloroformate and N-methylmorpholine. After 2 hours at −20° C. and an additional hour at ambient temperature, the reaction was quenched with 2N aqueous potassium bicarbonate. The product was extracted into ethyl acetate, washed with 1M aqueous citric acid, and saturated sodium bicarbonate. The organic phase was dried over anhydrous sodium sulfate. Filtration $N^\alpha$-t-butyloxycarbonyl-$N^{im}$-benzyloxycarbonyl-L-histidyl-glycine amide.

The product was dissolved in anhydrous methanolic hydrogen chloride (saturated at 0° C.) for 30 minutes, followed by removal of solvent under reduced pressure, forming $N^{im}$-benzyloxycarbonyl-L-histidyl-glycine amide. This was dissolved in tetrahydrofuran, and isobutyl chloroformate, N-methylmorpholine, and $N^\alpha,N^\epsilon$-dibenzyloxycarbonyl-L-lysyl-L-histidyl-glycine amide (3 hours at −20° C., then 1 hour at ambient temperature). This product was then dissolved in glacial acetic acid and hydrogenated overnight in the presence of 10% Pd-C catalyst. The resultant L-lysyl-L-histidyl-glycine amide was lyophilized from water several times, then purified by liquid chromatography on a C-18 reverse-phase column to yield the desired tripeptide amide as a triacetate salt.

EXAMPLE 8

Synthesis of L-lysyl-L-histidyl-glycine octyl ester

Glycine, octyl alcohol, p-toluenesulfonic acid monohydrate, and benzene were refluxed together over a period of 24 hours using a Dean-Stark trap to azeotropically remove the evolved water. After cooling to room temperature and then adding dry ethyl ether, octyl glycinate p-toluenesulfonate salt was collected by suction filtration. The salt was treated with saturated sodium bicarbonate solution and extracted into dichloromethane. Evaporation gave the free amine, which was redissolved in dry tetrahydrofuran (THF) and added to a stirring solution of $N^\alpha$-t-butyloxycarbonyl-$N^{im}$-benzyloxycarbonyl-L-histidine, N-methylmorpholine, and isobutyl chloroformate in dry THF at −20° C. After 2 hours at −20° C. and an additional hour at ambient temperature, the reaction was quenched with 2N aqueous potassium bicarbonate. The product was extracted into ethyl acetate, washed with 1M citric acid, and saturated sodium bicarbonate. The organic phase was dried over anhydrous sodium sulfate, filtered and evaporate.

The resulting fully protected dipeptide ester was treated with 30% trifluoroacetic acid in dichloromethane at ambient temperature for 40 minutes, neutralized with saturated aqueous sodium bicarbonate solution, and extracted into ethyl acetate.

Evaporation gave the partially deprotected dipeptide, which was redissolved in dry THF and added to a stirring solution of $N^\alpha,N^\epsilon$-dibenzyloxycarbonyl-L-lysine, N-methylmorpholine and isobutyl chloroformate in dry THF at $-20°$ C. The formed, fully protected tripeptide ester was totally deprotected by treatment with hydrogen gas in glacial acetic acid at ambient temperature in the presence of 10% Pd-C catalyst. Filtration through a layer of Celite, lyophilization from water, and purification by liquid chromatography on a C-18 reverse-phase column gave the desired tripeptide ester as its triacetate salt.

EXAMPLE 9

Synthesis of L-lysyl-L-histidyl-glycyl-L-valyl-L-phenylalanyl-L-valine

Multi-gram quantity of L-lysyl-L-histidyl-glycyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as coupling agent (2 hours at $-20°$ C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, t-butyloxycarbonylglycine, $N^\alpha$-t-butyloxycarbonyl-$N^{im}$-benzyloxycarbonyl-L-histidine, $N^\alpha,N^\epsilon$-dibenzyloxycarbonyl-lysine) were added in sequential order to obtain the desired peptide. The final peptide was completely deprotected using hydrogen gas in glacial acetic acid for 5 days in the presence of 10% Pd-C catalyst. The final peptide was lyophilized from water and purified by liquid chromatography on a C-18 reverse-phase column to produce the desired hexapeptide in multi-gram quantity.

The above systematic synthesis proved advantageous over some of the solid phase methods in providing multi-gram quantity of the desired in high purity with minimal purification.

EXAMPLE 10

Stimulation of hair growth in mice by subdermal injection of glycyl-L-histidyl-L-lysyl-L-valyl-L-phenylalanyl-L-valine:copper(II)

To demonstrate the stimulation of hair growth in warm-blooded animals, the backs of mice were shaved on day 1 using an electric shaver. Increasing doses of glycyl-L-histidyl-L-lysyl-L-valyl-L-phenylalanyl-L-valine:copper(II) in aqueous solution was infiltrated under the skin in two locations. Mice are examined daily for signs of hair growth in the shaved area and at the injection sites. Injection with glycyl-L-histidyl-L-lysyl-L-valyl-L-phenylalanyl-L-valine:copper(II) stimulated hair growth at and around the injection site by days 14-21. Such accelerated hair growth is in excess of normal regrowth of hair in the shaved area. Hair growth at both injection sites is considered a positive response.

A series of experiments are summarized in Table 1. A positive response was observed in 80-90% of the mice injected with the glycyl-L-histidyl-L-lysyl-L-valyl-L-phenylalanyl-L-valine:copper(II) solution compared to no response in mice injected with saline.

TABLE 1

| DOSE (mg/inj.) | % POS. RESPONSE |
|---|---|
| 0.10 | 86 (n = 7) |
| 0.25 | 89 (n = 9) |
| 0.50 | 89 (n = 54) |
| 1.00 | 95 (n = 20) |
| Saline | 0 (n > 50) |

Following injection of glycyl-L-histidyl-L-lysyl-L-valyl-L-phenylalanyl-L-valine:copper(II), indications of hair growth were seen within 10 days. The first visual signs are a darkening of the skin in a circular region surrounding the injection site. The size of this region is generally dose dependent, increasing with an increase in dose. A 0.5 mg injection will usually produce a circle of growth measuring approximately 0.5 cm in diameter. Active hair growth takes place between 14-20 days with a maximum effect seen by day 28.

Figure 2:
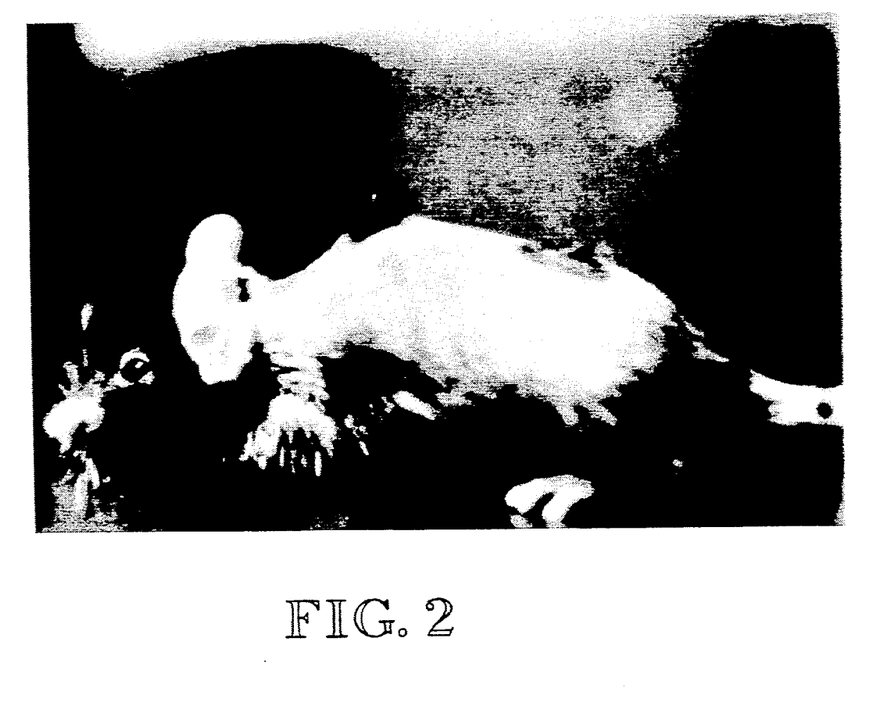
FIG. 2 is a photograph of a mouse injected with a glycyl-L-histidyl-L-lysyl-L-valyl-L-phenylalanyl-L-valine:copper(II) solution showing accelerated hair growth at two injection sites and the lack of hair growth in surrounding shaved areas.
Figure 3:
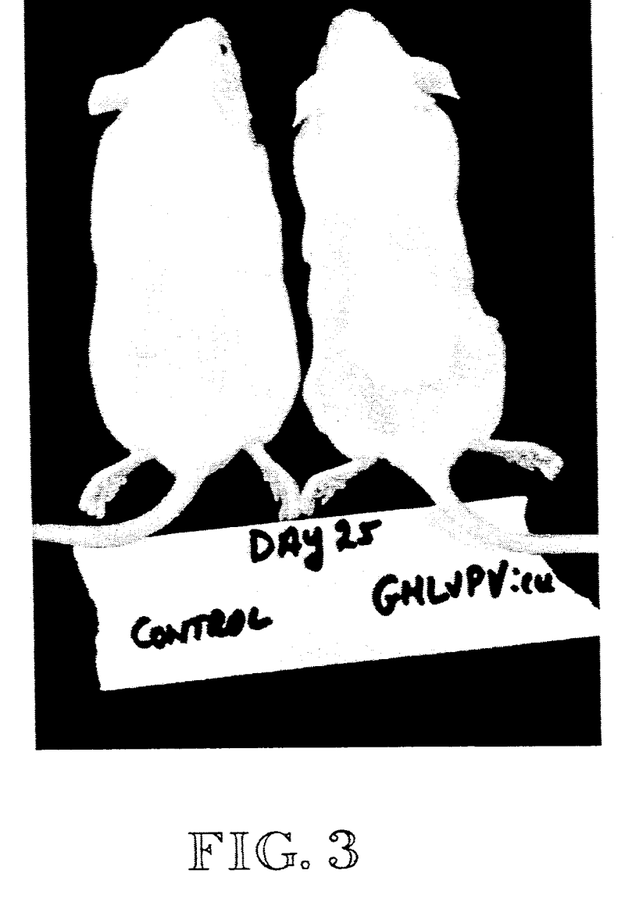
FIG. 3 is a photograph of a control mouse injected with saline (left mouse) and a mouse injected with a glycyl-L-histidyl-L-lysyl-L-valyl-L-phenylalanyl-L-valine:copper(II) solution showing accelerated hair growth (right mouse), both at 25 days from the date of injection.

FIG. 2 is a photograph of a mouse injected with glycyl-L-histidyl-L-lysyl-L-valyl-L-phenylalanyl-L-valine:copper(II) solution showing accelerated hair growth at two injection sites and the lack of hair growth in surrounding shaved areas. FIG. 3 is a photograph of a control mouse injected at a single site with saline (left mouse) and a mouse injected at a single site with glycyl-L-histidyl-L-lysyl-L-valyl-L-phenylalanyl-L-valine:copper(II) solution showing accelerated hair growth (right mouse), both at 25 days from the date of injection.

Figure 4:
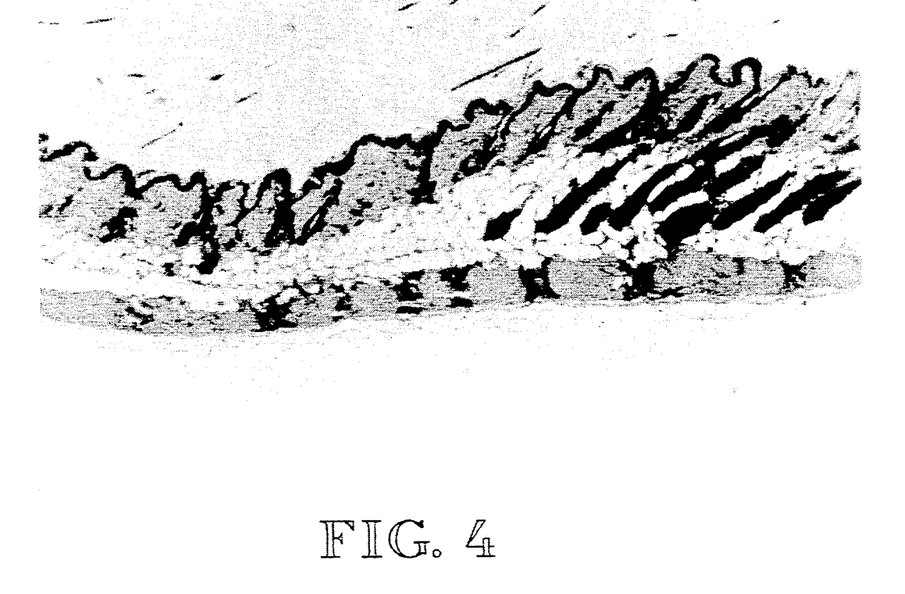
FIG. 4 is a photomicrograph which illustrates the histological section from a mouse injected with glycyl-L-histidyl-L-lysyl-L-valyl-L-phenylalanyl-L-valine:-copper(II).

Histological sections of skin biopsies taken through the site of injection reveal anagen state follicles. A skin biopsy was taken through the area of accelerated hair growth, imbedded in parafin, sectioned, and stained for histological evaluation. Microscopic examination of the resulting slide revealed that the follicles extend deep into the subcutaneous fat layer. Moreover, the surrounding skin contains telogen state follicles resting in the dermal layer, and a gradation of effect is observed as you move closer to the injection site. There is also a thickening of the fat layer with a deepening of follicle projection nearer to the injection sites. FIG. 4 is a photograph which illustrates the histological section from a mouse injection with glycyl-L-histidyl-L-lysyl-L-valyl-L-phenylalanyl-L-valine:copper(II). The area of injection is on the right side of the photograph. A decrease in hair follicle density and the subcutaneous fat layer is observed at increasing distance from the injection site.

EXAMPLE 11

Stimulation of hair growth in mice by subdermal injection of glycyl-L-histidyl-L-lysine octyl ester:metal ion (II) complexes Mice were shaved and injected in two locations with an aqueous solution of glycyl-L-histidyl-L-lysine octyl ester:metal ion (GHL octyl:metal ion) at a ratio of peptide to metal ion of 2:1. A dose of 500 micrograms was injected per mouse.

Hair growth at both injection sites is considered a positive response. The results of the experiment are summarized in Table 2. There was a significant acceleration of hair growth within 2 to 3 weeks following the injection. Mice injected with saline did not show an acceleration of hair growth.

TABLE 2

| COMPLEX | POSITIVE RESPONSE (No. Positive/Total No.) |
|---|---|
| GHL Octyl:Cu(II) | 4/4 |
| GHL Octyl:Cd(II) | 2/4 |
| GHL Octyl:Co(II) | 4/4 |
| GHL Octyl:Sn(II) | 2/4 |
| GHL Octyl:Fe(II) | 2/4 |
| GHL Octyl:Mg(II) | 2/4 |

EXAMPLE 12

Stimulation of hair growth in mice by subdermal injection of L-lysyl-L-histidyl-glycine octyl ester:copper(II) and L-lysyl-L-histidyl-glycyl-L-valyl-L-phenylalanyl-L-valine:copper(II)

Mice were shaved and injected in two locations with an aqueous solution of L-lysyl-L-histidyl-glycine octyl ester:copper(II) (LHG Octyl:Cu) and L-lysyl-L-histidyl-glycyl-L-L-valyl-L-phenylalanyl-L-valine:Cu (LGHVFV:Cu) at a ratio of peptide to metal ion of 2:1, and at a dose of 500 and 1000 micrograms per mouse. Hair growth at both injection sites is considered a positive response. There was a significant acceleration of hair growth within 2-3 weeks following the injection. Mice injected with saline did not show an acceleration. The results of this experiment are summarized in Table 3.

TABLE 3

| COMPOUND | DOSE | POSITIVE RESPONSE (No. Positive/Total No.) | |
|---|---|---|---|
| LHG-Octyl:Cu | 0.5 mg | 8/8 | 100% |
| | 1.0 mg | 5/5 | 100% |
| LHGVFV:Cu | 0.5 mg | 9/10 | 90% |
| | 1.0 mg | 5/5 | 100% |

EXAMPLE 13

Stimulation of hair growth in mice by topical application of glycyl-L-histidyl-L-lysyl-L-valyl-L-phenylalanyl-L-valine:copper(II)

To demonstrate hair growth after topical application of a pharmaceutical composition containing a peptide-metal ion composition of the present invention, mice were shaved and treated daily with the following pharmaceutical composition containing glycyl-L-histidyl-L-lysyl-L-valyl-L-phenylalanyl-L-valine:copper(II) (GHLVFV:Cu) at a ratio of peptide to metal ion of 2:1.

| GHLVFV:Cu | 1% (w/w) |
|---|---|
| Nonocynol-9 | 5% |
| Unibase Cream | 94% |

Hair growth at the treated site is considered a positive response. Four of the five mice (80%) treated with the topical composition showed accelerated hair growth in the area of topical application.

EXAMPLE 14

Stimulation of hair growth in mice by subdermal injection of glycyl-L-(3-methyl)-histidyl-L-lysyl-glycyl-L-tryptophan:copper(II)

Mice were shaved and injected intradermally in two locations with various doses of glycyl-L-(3-methyl)-histidyl-L-lysyl-glycyl-L-tryptophan:copper(II). Hair growth was noted in the mice within 2-3 weeks following the injections. Hair growth at both injection sites is considered a positive response. The results are presented in Table 4.

TABLE 4

| DOSE | POSITIVE RESPONSE (No. Positive/Total No.) | |
|---|---|---|
| Exp. 1 500 mg | 5/5 | 100% |
| Exp. 2 250 mg | 5/5 | 100% |

EXAMPLE 15

Figure 5:
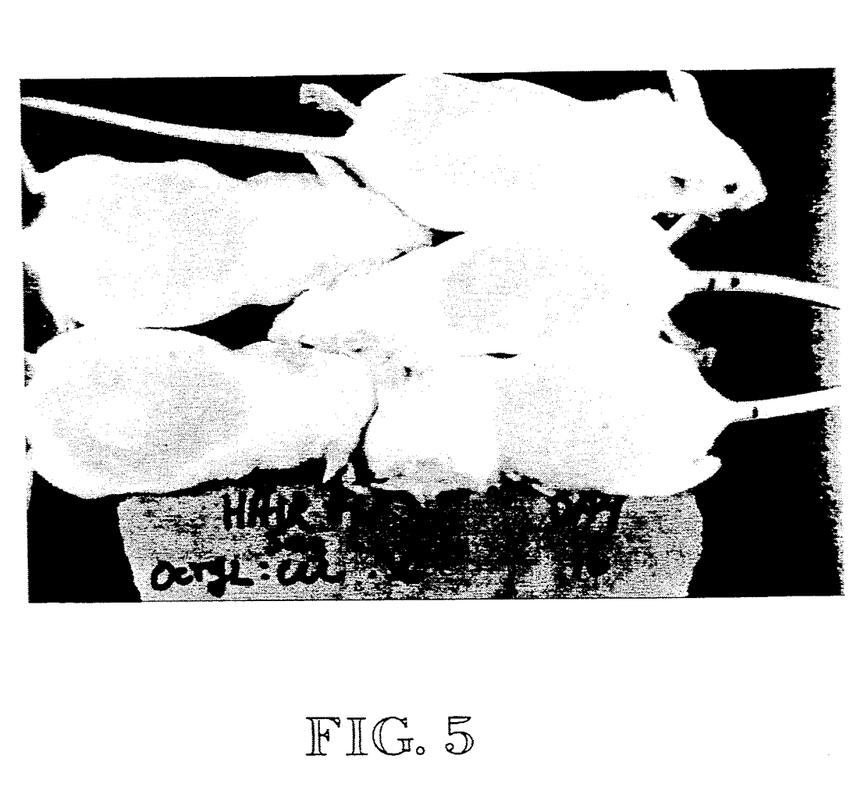
FIG. 5 is a photograph of injected with glycyl-L-histidyl-L-lysine n-octyl ester:copper(II) showing significant acceleration of hair growth within 2-3 weeks following injection.

Use of glycyl-L-histidyl-L-lysine n-octyl ester:copper(II) to stimulate hair growth in mice Mice were shaved and injected once with glycyl-L-histidyl-L-lysine n-octyl ester:copper(II) at a dose of 500 micrograms per mouse. FIG. 5 shows that there was a significant acceleration of hair growth within 2-3 weeks following injection of 500 micrograms. Mice injected with saline did not show an acceleration.

Figure 6:
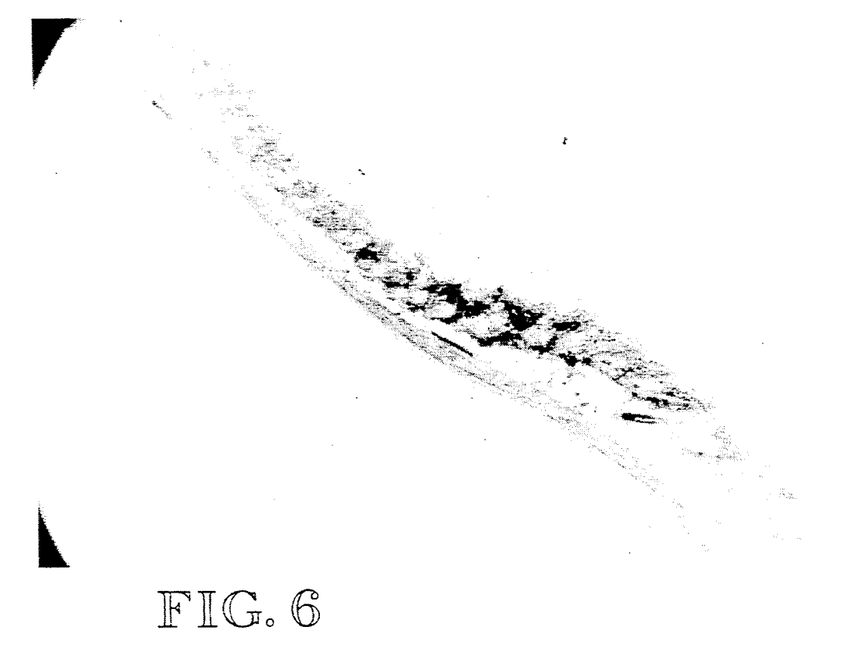
FIG. 6 is a photomicrograph of a biopsy sample at day 21 illustrating the increase in fat layer following injection with glycyl-L-histidyl-L-lysine n-octyl ester:-copper(II).

In the region of accelerated hair growth, there was a significant increase in the thickness of the subcutaneous fat layer. It is known that the thickness of this fat layer is directly associated with hair growth. This increase in subcutaneous fat is shown by taking a biopsy sample at day 21 through the area and sectioning for histology slides. FIG. 6 shows this increase in fat layer. The injected area is on the right with the adjacent uninjected area on the left of the photograph. There was an obvious increase in both the number and size of the fat cells. Measurements demonstrate that there is an approximately threefold increase in the subcutaneous fat layer in the skin near the injection site.

EXAMPLE 16

Figure 7:
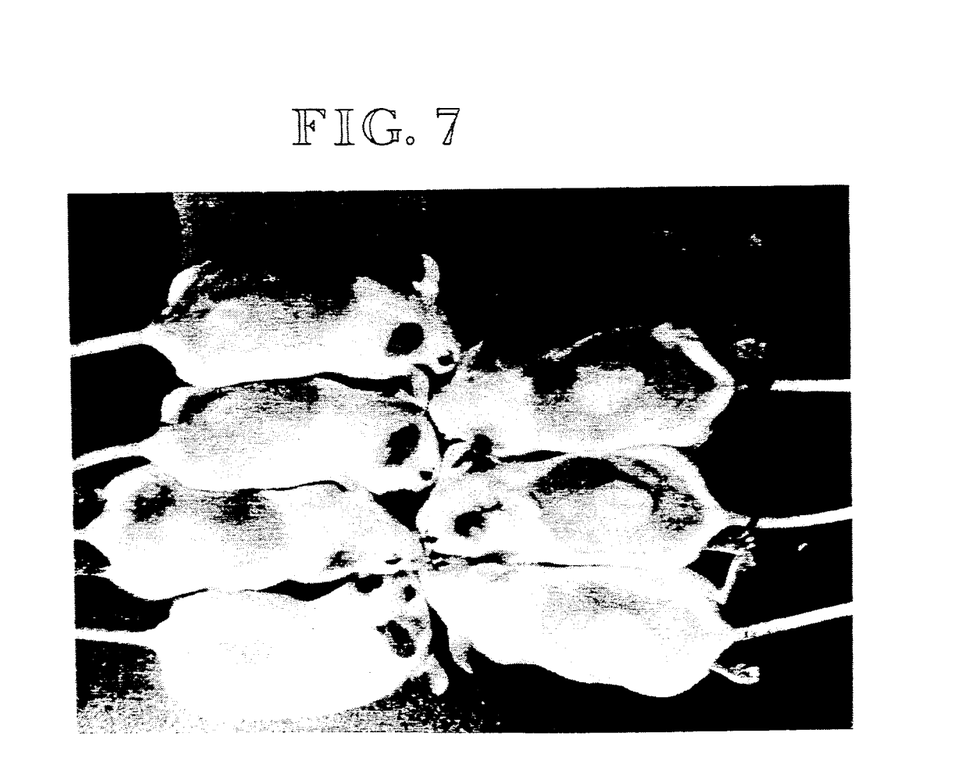
FIG. 7 is a photograph of mice injected with glycyl-L-histidyl-L-lysine decyl ester:copper(II) illustrating stimulated hair growth.
Figure 8:
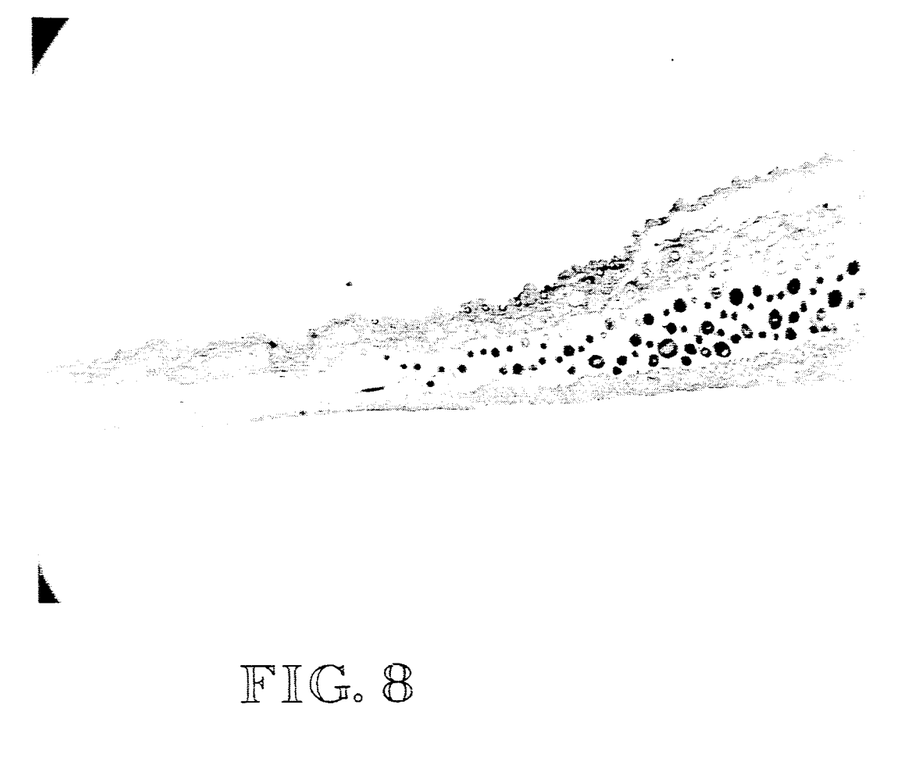
FIG. 8 is a photomicrograph of a biopsy samply taken from a mouse injected with glycyl-L-histidyl-L-lysine decyl ester:copper(II) illustrating a marked proliferation of hair shafts within the subcutaneous fat layer of the area exhibiting accelerated hair growth.

Use of glycyl-L-histidyl-L-lysine decyl ester:copper(II) to stimulate hair growth in mice A group of ten mice were shaved and injected once with glycyl-L-histidyl-L-lysine decyl ester:copper(II) at a dose of 500 micrograms per mouse. FIG. 7 shows that there was a significant acceleration of hair growth within 2-3 weeks following the injection. Microscopic examination also provided evidence of increased hair growth, fat cell layer and increased hair follicle density in the area surrounding the injection site. FIG. 8 shows that there is a marked proliferation of hair shaft units which appear within the subcutaneous fat layer of the area of accelerated growth. Examination of the skin distant from the injection site showed a normal histology.

EXAMPLE 17

Figure 9A:
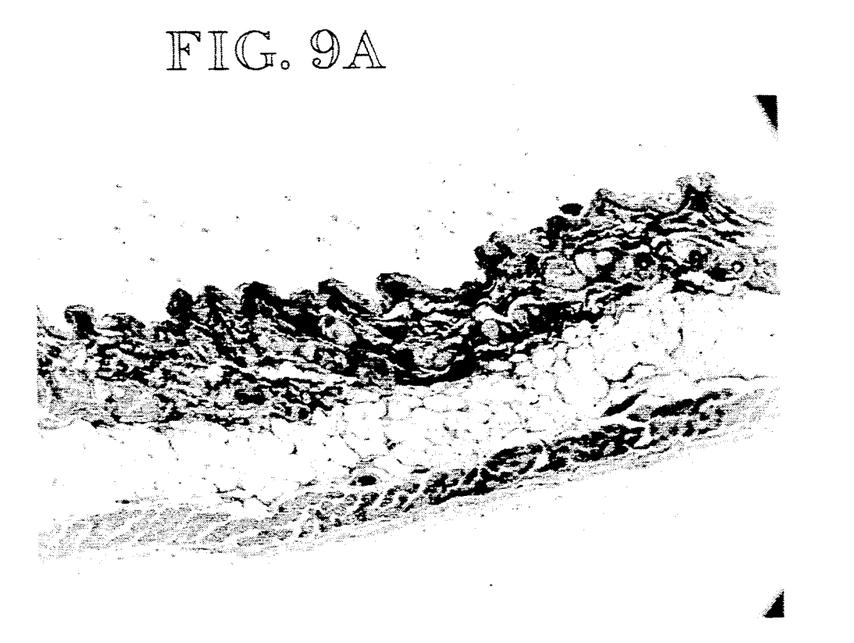
Figure 9B:
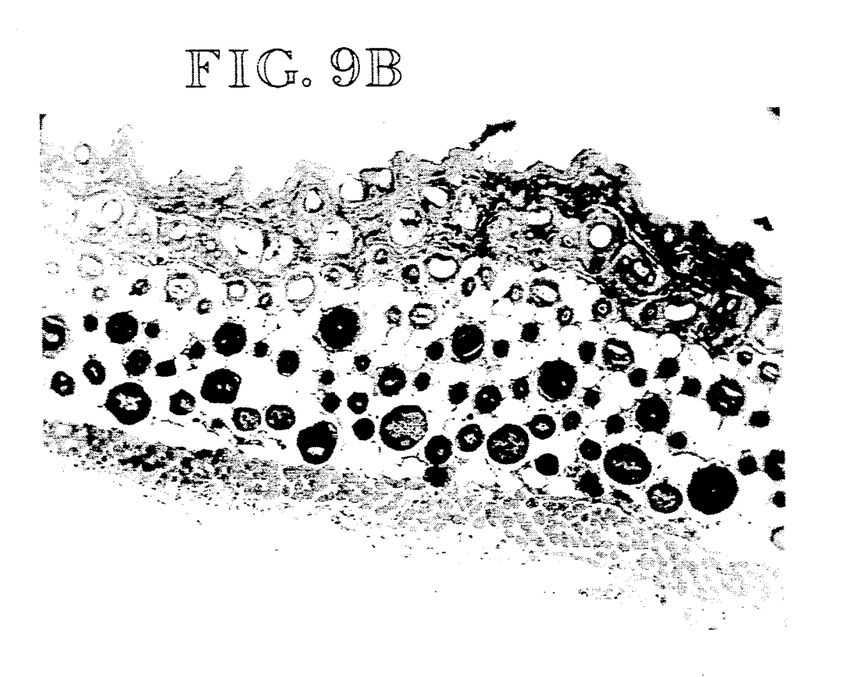

Use of glycyl-L-histidyl-L-lysine palmityl ester:copper(II) to stimulate hair growth in mice A group of 10 mice were shaved and injected once with glycyl-L-histidyl-L-lysine palmityl ester:copper- (II) at a dose of 500 micrograms per mose. There was a significant accelerlation of hair growth within 2-3 weeks following the injection. Histological sections through the area of accelerated hair growth were similar to those described above. This is shown in FIG. 9. The photomicrograph demonstrates (FIG. 9B) the large number of developing hair follicles within the subcutaneous fat layer, similar to that seen following the glycyl-L-histidyl-L-lysine decyl ester:copper(II) injection, while the photomicrograph of a histological section through a non-treated area (FIG. 9A) does not reveal such hair follicle development.

I claim:

1. A metal-peptide having the general formula:

glycyl-L-histidyl-L-lysine:X wherein X is a metal ion selected from the group consisting of cadmium(II), cobalt(II), tin(II), iron(II) and manganese(II).

2. A metal-peptide derivative of GHL-X having the general formula:

$$[\text{glycyl-L-histidyl-L-lysine-C}-R]\text{:X}$$

wherein
X is a metal ion selected from the group consisting of cadmium(II), cobalt(II), tin(II), iron(II) and manganese(II); and
R is selected from the group consisting of an —NH$_2$ moiety, alkyl moieties containing from 1 to 18 carbon atoms, aryl moieties containing from 6 to 12 carbon atoms, alkoxy moieties containing from 1 to 18 carbon atoms, aryloxy moieties containing from 6 to 12 carbon atoms, and alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-2.

3. A metal-peptide derivative of GHL-Cu having the general formula:

$$[\text{glycyl-L-histidyl-L-lysine-C}-R]\text{:copper(II)}$$

wherein R is an alkylamino moiety containing from 1 to 18 carbon atoms, L-tryptophan or (glycyl)$_n$-L-tryptophan where n=1-2.

4. A metal-peptide having the general formula:

glycyl-L-(3-methyl)-histidyl-L-lysine:X wherein X is a metal ion selected from the group consisting of copper(II), cadmium(II), cobalt(II), tin(II), iron(II) and manganese(II).

5. A metal-peptide derivative of glycyl-L-(3-methyl)-histidyl-L-lysine:X having the general formula:

$$[\text{glycyl-L-(3-methyl)-histidyl-L-lysine-C}-R]\text{:X}$$

wherein
X is a metal ion selected from the group consisting of copper(II), cadmium(II), cobalt(II), tin(II), iron(II) and manganese(II); and
R is selected from the group consisting of an —NH$_2$ moiety, alkyl moieties containing from 1 to 18 carbon atoms, aryl moieties containing from 6 to 12 carbon atoms, alkoxy moieties containing from 1 to 18 carbon atoms, aryloxy moieties containing from 6 to 12 carbon atoms, alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-2.

6. A metal-peptide having the general formula:

L-lysyl-L-histidyl-glycine:X wherein X is a metal ion selected from the group consisting of copper(II), cadmium(II), cobalt(II), tin(II), iron(II) and manganese(II).

7. A metal-peptide derivative of LHG-X having the general formula:

$$[\text{L-lysyl-L-histidyl-glycine-C}-R]\text{:X}$$

wherein
X is a metal ion selected from the group consisting of copper(II), cadmium(II), cobalt(II), tin(II), iron(II) and manganese(II); and
R is selected from the group consisting of an —NH$_2$ moiety, alkyl moieties containing from 1 to 18 carbon atoms, aryl moieties containing from 6 to 12 carbon atoms, alkoxy moieties containing from 1 to 18 carbon atoms, aryloxy moieties containing from 6 to 12 carbon atoms, and alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-2.

8. A metal-peptide having the general formula:

L-lysyl-L-(3-methyl)-histidyl-glycine:X wherein X is a metal ion selected from the group consisting of copper(II), cadmium(II), cobalt(II), tin(II), iron(II) and manganese(II).

9. A metal-peptide derivative of L-lysyl-L-(3-methyl)-histidyl-glycine:X having the general formula:

$$[\text{L-lysyl-L-(3-methyl)-histidyl-glycine-C}-R]\text{:X}$$

wherein
X is a metal ion selected from the group consisting of copper(II), cadmium(II), cobalt(II), tin(II), iron(II) and manganese(II); and
R is selected from the group consisting of an —NH$_2$ moiety, alkyl moieties containing from 1 to 18 carbon atoms, aryl moieties containing from 6 to 12 carbon atoms, alkoxy moieties containing from 1 to 18 carbon atoms, aryloxy moieties containing from 6 to 12 carbon atoms, and alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-2.

10. The metal-peptide of any one of claims 1–9 further including a vehicle which adapts the metal-peptide for intradermal injection or topical application to a warm-blooded animal.

* * * * *